United States Patent [19]

Hagemann

[11] 3,941,873

[45] Mar. 2, 1976

[54] PROCESS FOR THE PREPARATION OF CARBONYL DIISOCYANATE

[75] Inventor: Hermann Hagemann, Cologne, Germany

[73] Assignee: Bayer Aktiengesellschaft, Leverkusen, Germany

[22] Filed: Feb. 11, 1975

[21] Appl. No.: 548,954

[30] Foreign Application Priority Data

Mar. 12, 1974 Germany............................ 2411674

[52] U.S. Cl................................. 423/365; 260/616
[51] Int. Cl.$^2$............................................ C01B 21/00
[58] Field of Search ............. 423/365, 364, 357, 416

[56] References Cited
FOREIGN PATENTS OR APPLICATIONS 1,266,288  4/1968  Germany............................ 423/365

OTHER PUBLICATIONS

Verbeck et al., "Preparation of Carbonyl and Fluorocarbonyl Psuedohalides in Molten Salts," Angew. Chem. Int. Ed. Engl. 6, (10), 871–872, (1967).

*Primary Examiner*—Earl C. Thomas
*Attorney, Agent, or Firm*—Joseph C. Gil; Gene Harsh

[57] ABSTRACT

This invention relates to a process for the preparation of carbonyl diisocyanate, $CO(NCO)_2$, which comprises reacting trichloroisocyanuric acid and/or an alkali metal salt of dichloroisocyanuric acid with phosgene at temperatures of from about 150° to about 200°C.

4 Claims, No Drawings

PROCESS FOR THE PREPARATION OF CARBONYL DIISOCYANATE

BACKGROUND OF THE INVENTION

It is known that compounds which contain positively-polarized chlorine atoms, such as N-chloro compounds, and compounds which contain negatively-polarized chlorine atoms, such as hydrochloric acid, may react with each other and split off chlorine in the process. These reactions generally require high temperatures or even equimolar quantities of Friedel/Crafts catalysts. Moreover, the reaction is not generally practicable and is often accompanied by side-reactions or secondary reactions so that it is impossible to predict the main reaction product.

It is also known, (DAS No. 1,266,288), to prepare carbonyl diisocyanate by the thermolysis of N-trichloroisocyanuric acid at a temperature of from 200° to 400°C, accompanied by the formation of $NCl_3$, in accordance with the following equation:

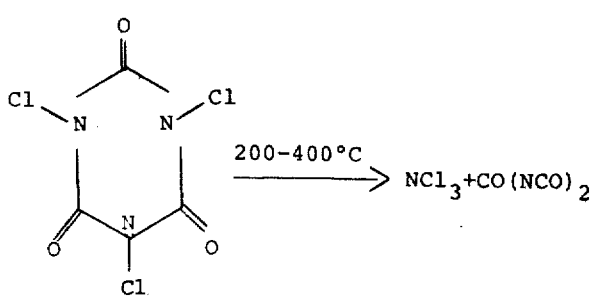

The reaction is accompanied by side-reactions and is difficult to control due to the simultaneous formation of the highly explosive compound, $NCl_3$.

Another process for the preparation of $CO(NCO)_2$ is the reaction of difluorophosgene with potassium cyanate in molten LiCl/KCl at temperatures of about 400°C. This method of preparation involves relatively high technical expenditure because of the low conversion rates and because of high reaction temperatures required, (Angew. Chem. 79, 860 (1967)).

DESCRIPTION OF THE INVENTION

It has now surprisingly been found that when phosgene is mixed with trichloroisocyanuric acid and/or an alkali metal salt of dichloroisocyanuric acid, conversion of phosgene to $CO(NCO)_2$ with elimination of chlorine will proceed almost quantitatively, in terms of the positively-polarized chlorine atoms, at temperatures as low as from about 150° to about 200°C, preferably from about 160° to about 180°C. The reaction is preferably carried out in a high boiling, inert organic solvent, such as trichlorobenzene or a o-dichlorobenzene.

According to a recent publication which describes the formation of trichloroacetyl isocyanate from trichloroacetyl chloride and trichloroisocyanuric acid, (Zh. Org. Khim. 9, (1973) 1815-18), it was to be expected that the present process would give rise to Cl—CO—NCO, at least as the main reaction product. It was surprisingly found, however, that the reaction product obtained did not contain any Cl—CO—NCO but consisted exclusively of $CO(NCO)_2$. Even when the N-chloro compound was only partly converted, no Cl—CO—NCO could be detected. This is surprising in view of the fact that, in phosgene, the first chlorine atom is normally substituted very much more rapidly than is the second chlorine atom. For example, there is no difficulty in preparing chloroformic acid esters by the reaction of phosgene and an alcohol.

Another surprising feature, which is also new, is that the sodium salt of dichloroisocyanuric acid may also be used in such a reaction. It was to be expected that a salt of this type would be very much less soluble in an inert organic solvent, such as chlorinated benzene, and that a reaction would, therefore, be very much more difficult or even impossible. For example, the trisodium salt of isocyanuric acid will not react with highly reactive acid chlorides, even in solvents such as adipic acid dinitrile and at elevated temperatures, because this salt is not sufficiently soluble in organic solvents.

The process according to the invention may be illustrated by the following reaction scheme:

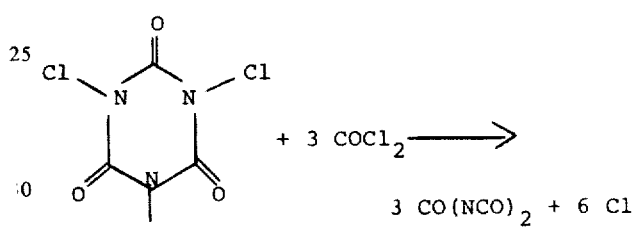

Instead of using trichloroisocyanuric acid, the present process may preferably be carried out using an alkali metal salt, most preferably the sodium or potassium salt, of dichloroisocyanuric acid.

The reaction may be carried out by generally suspending the isocyanuric acid derivative in a solvent and then passing phosgene through the resulting suspension. The reaction product distills over at the reaction temperature and is obtained in a pure form by fine careful distillation.

The volume/time yield is particularly high when the monosodium salt of dichloroisocyanuric acid is used.

Carbonyl diisocyanate is an exceptionally highly reactive diisocyanate. For example, it reacts, even at room temperature, with the smallest traces of moisture present in inert solvents. It is therefore, an ideal dehydrating agent for preparing absolute solvents. Carbonyl diisocyanates differs advantageously from known dehydrating agents, for example, those used for the preparation of absolute ether, (e.g. metallic sodium or phosphorous pentoxide), by virtue of the fact that it is miscible in any proportions with the solvent which is to be dehydrated. One disadvantage of known dehydrating agents is that their active surface is, to a large extent, inactivated, (e.g. by the sodium hydroxide formed or by a so-called "skin" of polyphosphoric acid), so that the dehydrating agent must be continuously renewed. Such disadvantage cannot occur when using the present product as the dehydrating agent. For example, in preparing absolute ether it is sufficient to add a suitable quantity of carbonyl diisocyanate to ether which has previously been partially dried over, for example, calcium chloride and then to keep the mixture at room temperature for a few minutes. The ether is then recovered, e.g. as by distillation. Although carbonyl diisocyanate is not a new compound, it may be said that the process according to this invention has enabled it to be obtained in a technically simple and economical manner.

EXAMPLE 1

44 g (0.2 mol) of the monosodium salt of dichloroisocyanuric acid, suspended in 150 ml trichlorobenzene, are introduced into a reaction vessel. Phosgene is slowly introduced with vigorous mixing, at a reaction temperature of about 180°C and the $CO(NCO)_2$ which is formed, with elimination of chlorine, is continuously distilled off.

18 g (80% of the theoretical yield, based on positively-polarized chlorine atoms) of $CO(NCO)_2$ are obtained after careful distillation. Bp.: 104°–106°C.

EXAMPLE 2

A stream of phosgene is slowly passed through a suspension of 120 g (0.545 mol) of monosodium dichloroisocyanurate in 350 ml o-dichlorobenzene at a reaction temperature of from 165° to 175°C with vigorous mixing. $CO(NCO)_2$ which is formed within about 4 hours under these conditions, and part of the chlorine liberated and the excess phosgene, as well as the o-dichlorobenzene which distills off under these conditions, are collected in an ice-cooled receiver.

Redistillation over an ice-cooled 30 cm packed column yields 57 g (93% of the theoretical yield, based on positively-polarized chlorine atoms) of $CO(NCO)_2$. Bp.: 104°–106°C.

EXAMPLE 3

About 10 g carbonyl diisocyanate are added at 20°C to 1 liter of diethyl ether previously dehydrated over calcium chloride. The mixture is maintained at room temperature for half an hour. The purified ether is then recovered by simple distillation in a carefully dried distillation apparatus. Metallic sodium is then extruded into the resulting dehydrated ether by means of a sodium press. The metallic surface of the sodium wire remained practically unchanged in its metallic appearance for 24 hours.

What is claimed is:

1. A process for the preparation of carbonyl diisocyanate comprising reacting trichloroisocyanuric acid and/or an alkali metal salt of dichloroisocyanuric acid with phosgene at a temperature of from about 150°C to about 200°C.

2. The process of claim 1, wherein the reaction is conducted in the presence of a high boiling, inert organic solvent.

3. The process of claim 2, wherein said solvent is selected from the group consisting of trichlorobenzene and o-dichlorobenzene.

4. The process of claim 1, wherein the reaction is conducted at a temperature of from about 160° to about 180°C.

* * * * *